United States Patent
Kunz et al.

(10) Patent No.: US 8,040,527 B2
(45) Date of Patent: Oct. 18, 2011

(54) REFRACTIVE PRODUCTION OF A CONCENTRICALLY FANNED STRUCTURED BUNDLE OF LIGHT BEAMS, OPTICAL, MEASURING DEVICE WITH REFRACTIVE DEFECTION ELEMENT

(75) Inventors: Martin Kunz, München (DE); Anton Schick, Velden (DE); Michael Stockmann, Bruckmühl (DE)

(73) Assignee: Siemens Aktiengesellschaft, Munich (DE)

( * ) Notice: Subject to any disclaimer, the term of this patent is extended or adjusted under 35 U.S.C. 154(b) by 110 days.

(21) Appl. No.: 12/525,361

(22) PCT Filed: Jan. 28, 2008

(86) PCT No.: PCT/EP2008/050929
§ 371 (c)(1),
(2), (4) Date: Jul. 31, 2009

(87) PCT Pub. No.: WO2008/092820
PCT Pub. Date: Aug. 7, 2008

(65) Prior Publication Data
US 2010/0020333 A1    Jan. 28, 2010

(30) Foreign Application Priority Data
Feb. 2, 2007  (DE) .......................... 10 2007 005 388

(51) Int. Cl.
*G01B 11/24* (2006.01)
(52) U.S. Cl. ............................ 356/603; 600/407; 348/47
(58) Field of Classification Search .................. 356/603, 356/635; 600/407; 348/47
See application file for complete search history.

(56) References Cited

U.S. PATENT DOCUMENTS

| | | | |
|---|---|---|---|
| 4,013,342 A * | 3/1977 | Narody | 385/18 |
| 6,751,494 B2 * | 6/2004 | Collier et al. | 600/407 |
| 7,436,525 B2 * | 10/2008 | Mukai et al. | 356/603 |
| 2002/0045811 A1 * | 4/2002 | Kittrell et al. | 600/407 |
| 2003/0164952 A1 | 9/2003 | Deichmann et al. | |
| 2004/0136010 A1 | 7/2004 | Jensen et al. | |

FOREIGN PATENT DOCUMENTS

| | | |
|---|---|---|
| CN | 1117379 A | 2/1996 |
| CN | 1897870 A | 1/2007 |

(Continued)

OTHER PUBLICATIONS

Changhe Zhou, Jia Jia, Liren Liu; "Circular Dammann Grating"; Optics Letters, vol. 28, No. 22, 2003, pp. 2174-2176.

(Continued)

*Primary Examiner* — Tarifur Chowdhury
*Assistant Examiner* — Isiaka Akanbi

(57) ABSTRACT

The invention describes an optical deflection element for the refractive production of a spatially structured bundle of light beams fanned concentrically to an optical axis of the deflection element. The optical deflection element has a base body made of optically transparent material, and has a light input and output side. The light input side is configured such that a primary bundle of light beams can be coupled in the base body. The light output side has a cylindrically symmetrical contour, which defines a recess in the base body. The fanning of the primary bundle of light beams is achieved by refraction on rotationally symmetric interfaces, which are variably inclined relative to the optical axis. The invention further relates to an optical measuring device for the three-dimensional measurement of a cavity in an object and a method for producing a concentrically fanned, spatially structured bundle of light beams.

19 Claims, 6 Drawing Sheets

FOREIGN PATENT DOCUMENTS

| | | |
|---|---|---|
| DE | 10231969 B4 | 9/2004 |
| DE | 102005034991 A1 | 4/2006 |
| DE | 102004058044 A1 | 6/2006 |
| GB | 1499359 | 2/1978 |
| GB | 1569614 | 6/1980 |
| WO | WO 9915930 A1 | 4/1999 |
| WO | 9939232 A1 | 8/1999 |
| WO | WO 02091915 A1 | 11/2002 |
| WO | WO 2004081492 A2 | 9/2004 |

OTHER PUBLICATIONS

Changhe Zhou et al., "Circular Dammann Grating"; Optics Letters, vol. 28, No. 22, 2003, pp. 2174-2176.

H. Dammann, E. Klotz: "Coherent optical generation and inspection of two-dimensional periodic structures", Optica Acta, 1977, vol. 24, No. 4, pp. 505-515.

\* cited by examiner

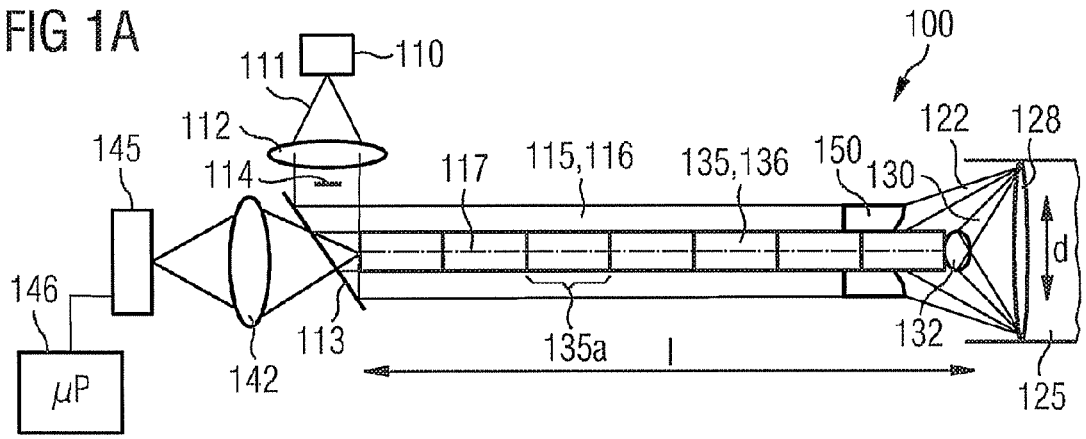
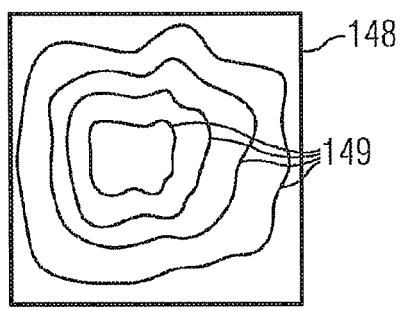
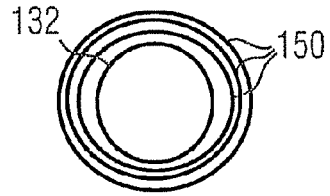
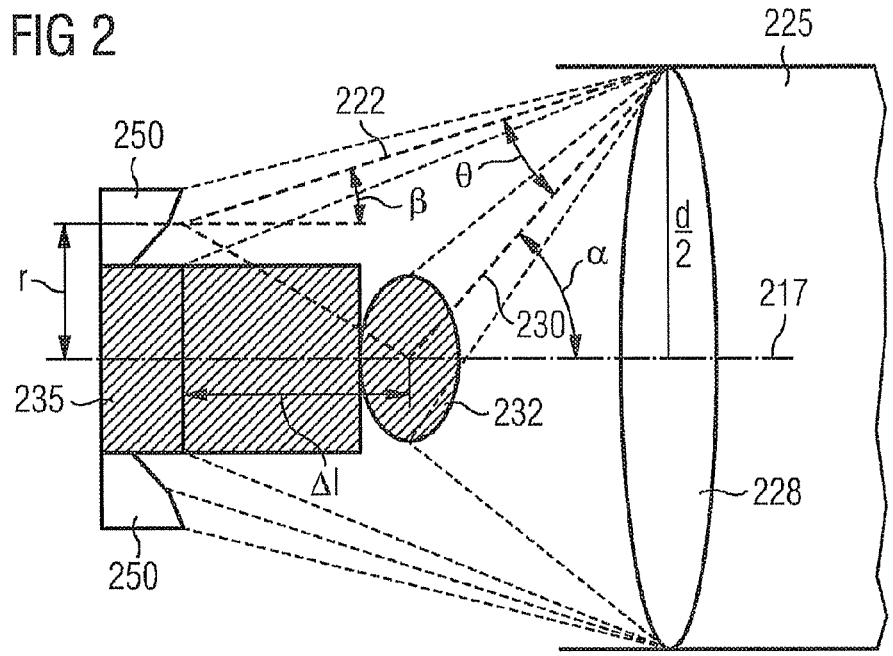

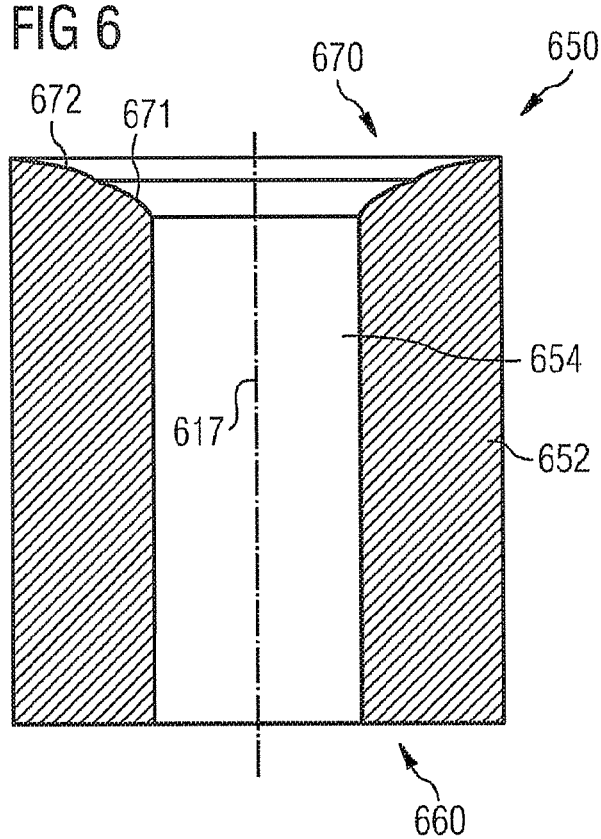
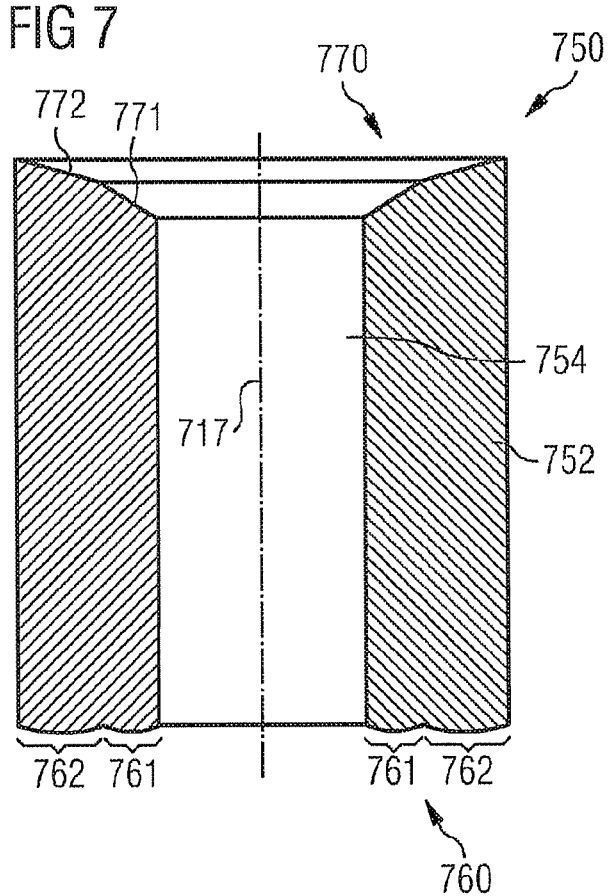

REFRACTIVE PRODUCTION OF A CONCENTRICALLY FANNED STRUCTURED BUNDLE OF LIGHT BEAMS, OPTICAL, MEASURING DEVICE WITH REFRACTIVE DEFECTION ELEMENT

CROSS REFERENCE TO RELATED APPLICATIONS

This application is the US National Stage of International Application No. PCT/EP2008/050929, filed Jan. 28, 2008 and claims the benefit thereof. The International Application claims the benefits of German application No. 10 2007 005 388.8 filed Feb. 2, 2007, both of the applications are incorporated by reference herein in their entirety.

FIELD OF THE INVENTION

The present invention relates to an optical deflection element, which can be used to fan a primary homogenous light beam bundle in the shape of a cone surface. The present invention also relates to an optical measuring device for the three-dimensional measuring of a cavity formed in an object, said optical measuring device comprising the above-mentioned optical deflection element. The present invention also relates to a method for producing a concentrically fanned, spatially structured light beam bundle using the above-mentioned optical deflection element.

BACKGROUND OF THE INVENTION

The surface structure of at least approximately tubular inner surfaces of a cavity can be captured three-dimensionally by means of optical triangulation. In this process a spatially structured illumination pattern is projected onto the inner surface of the respective cavity to be captured and the scene is captured digitally by means of a camera system. By measuring the distortion of the illumination pattern projected onto the inner wall as a result of the surface shape, which can be done automatically using known image processing methods, it is possible to calculate a digital model, which maps the shape of the cavity. Deviations and/or distortions of the captured projected lines from the known, initially symmetrical circular shapes that were concentric to an optical axis are captured in this process.

Such a cavity measurement by means of optical triangulation can advantageously be used when measuring or profiling the human auditory canal. The anatomy of the auditory canal means that an optical measuring device must be provided, which cannot exceed a maximum diameter of 4 mm. This basic condition applies to the entire object-side optical system of such a measuring device, said optical system having to be inserted into the auditory canal. The object-side optical system here comprises at least a camera system and an optical element for producing the structured illumination. The camera system and the optical element are disposed concentrically to a common optical axis of the optical measuring device here.

It is known that diffractive optical elements can be used to produce structured illumination. In particular (binary) phase gratings, also known as so-called Dammann gratings, can distribute the incident intensity of a primary light beam bundle selectively and in some instances largely uniformly to specific orders of diffraction due to a particularly advantageous substructure.

A so-called circular Dammann grating for producing a structured illumination pattern from concentric rings is known from the publication "Changhe Zhou, Jia Jia, Liren Liu; *Circular Dammann Grating; Optics Letters*, Vol. 28, No. 22, 2003, pages 2174-2176". However this has the disadvantage that it is difficult to achieve larger deflection angles in relation to the optical axis of the circular phase grating. It is true that larger deflection angles would in principle be possible using extremely small phase grating structures in the region of 150 mm but such small phase grating structures are technologically extremely difficult to produce. To produce such fine gratings, etching processes are needed which require much finer structuring than the etching processes currently used with a best resolution of 400 nm.

SUMMARY OF THE INVENTION

The object of the invention is to create an optical deflection element, which allows broad fanning of a primary light beam bundle and which can also be produced in a comparatively simple manner.

This object is achieved by the subject matter of the independent claims. Advantageous embodiments of the present invention are described in the dependent claims.

The first independent claim describes an optical deflection element for the refractive production of a spatially structured light beam bundle that is fanned concentrically to an optical axis of the deflection element. The optical deflection element has a base body, which is made at least partially of an optically transparent material and which has a light input side and a light output side. The light input side is configured such that a primary light beam bundle can be coupled into the base body. In relation to the optical axis of the deflection element the light output side has a cylindrically symmetrical contour, which defines a recess in the base body.

The described optical deflection element is based on the knowledge that it is possible to realize comparatively broad beam fanning in a simple manner by means of refraction at the corresponding optical interface due to a concave, i.e. inward curving, cylindrically symmetrically shaped contour on the output side. In this process the angle formed by the respective radial region of the contour with the optical axis determines the degree of spatial fanning according to Snellius's law of refraction.

The described optical deflection element can be produced with considerably less manufacturing outlay than known diffractive optical elements. In addition to conventional mechanical production methods, pressure methods are also suitable and these should be considered as suitable for economical mass production in particular.

According to one exemplary embodiment of the invention, the contour has a first annular section, which essentially has the shape of at least part of a first lateral surface of a cone pointing into the interior of the base body. The lateral lines of the first lateral surface form a first angle with the optical axis here.

If the contour essentially has the shape of a complete cone surface, the above-mentioned condition of a cylindrically symmetrical contour is automatically satisfied. If the contour has the shape of an incomplete cone surface, the above-mentioned condition of a cylindrically symmetrical contour is satisfied if the contour has the shape of the lateral surface of a truncated cone.

The term lateral lines here refers to those lines that run on the surface of the cone, which represents a rotational body, longitudinally in relation to its axis of rotation. The axis of rotation corresponds to the optical axis of the deflection element and/or base body here. The lateral lines are therefore the connecting lines between the actual or virtual tip of the cone or truncated cone and the peripheral points of the corresponding base circle.

The first angle described above between the lateral lines and the optical axis here is precisely half the size of the acceptance angle of the cone pointing into the interior of the base body. It is possible to determine the angular deflection and therefore the degree of fanning of the light cone exiting from the light exit surface by selecting the acceptance angle for the cone.

According to a further exemplary embodiment of the invention the contour has a second annular section, which is disposed outside the first annular section in a radial direction and which essentially has the shape of a second lateral surface of a truncated cone. The lateral lines of the second lateral surface here form a second angle with the optical axis, this second angle being different from the first angle.

The described annular sections thus represent different concentrically disposed, essentially conical facets. Each facet fans the primary light beam bundle as a function of the acceptance angle of the cone and the refractive index of the base body material with a specific acceptance angle in a cylindrically symmetrical manner. The light beam bundle exiting from the light exit surface therefore has two light structures with the shape of a cone surface, which have a different acceptance angle. In the case of a cylindrical cavity, which is oriented parallel and concentrically to the optical axis, it is thus possible to produce circular projection lines on the inner wall of the cylindrical cavity.

According to a further exemplary embodiment of the invention the contour has at least a third annular section, which is disposed outside the second annular section in a radial direction and which essentially has the shape of a third lateral surface of a truncated cone. The lateral lines of the third lateral surface form a third angle with the optical axis here, this third angle being different from the second angle.

The third angle is also preferably different from the first angle, so that all the light structures with the shape of a cone surface, which exit from the light exit surface, have a different acceptance angle.

It should be noted that the cylindrically symmetrical contour can also be divided into more than three annular sections. It is thus possible for the primary light beam bundle coupled in on the light input side in principle to be spatially structured to any degree of fineness, so that a plurality of light structures with the shape of a cone surface can be produced in a simple manner.

By using a number of light structures with the shape of a cone surface when measuring the human auditory canal it is possible to tailor the structure of the overall illumination pattern effectively to the expected shape of an auditory canal to be measured. The projection of a number of concentric rings at different angles to the optical axis onto the inner wall of the auditory canal should be considered to be particularly appropriate here. In order to achieve a sufficiently large triangulation angle in an optical measuring device, ensuring a local resolution of 50 µm in all spatial directions, as required for many applications, illumination angles in the region of 10° to 30° are required in relation to the optical axis. Such illumination angles can be achieved without any problem using the described optical deflection element. The triangulation angle is defined as usual by the angular distance between the beam path of the illumination light and the beam path of the measuring light captured by the camera.

According to a further exemplary embodiment of the invention the angular difference between the first angle and a right angle is greater than the angular difference between the second angle and a right angle. This means that the outer conical facets have a flatter inclination in relation to a cross-sectional plane oriented perpendicular to the optical axis than the inner conical facets.

The described configuration of the different conical facets with graduated angles of inclination has the advantage that the optical deflection element can be produced particularly simply. The configuration of the cylindrically symmetrical recess here can be achieved by two-stage machining, in which (a) a first conical recess with a small acceptance angle is assigned to the first annular section and (b) a second conical recess with a large acceptance angle is assigned to the second annular section. The sequence of the machining steps (a) and (b) is immaterial here.

It should be noted that a gradual increase in the described angular differences for the individual annular sections can also be realized in a corresponding manner from the outside inward, i.e. toward the optical axis, with more than three annular sections.

According to a further exemplary embodiment of the invention the angular difference between the first angle and a right angle is smaller than the angular difference between the second angle and a right angle. This means that the outer conical facets have a steeper inclination in relation to a cross-sectional plane to the optical axis than the inner conical facets.

The graduated angles of inclination described with this exemplary embodiment have the advantage that those light beams exiting from the light output side of the base body at the lateral surfaces of the outer annular section are refracted further away from the optical axis than those light beams exiting from the light output side of the base body at the lateral surfaces of annular sections further in. The beam paths of the individual light structures exiting from the light output side therefore do not cross, so the pattern of the individual beam paths is particularly clear.

According to a further exemplary embodiment of the invention the first annular section has the shape of at least part of a first lateral surface of a cone pointing into the interior of the base body, the second annular section has the shape of a second lateral surface of a truncated cone and/or the third annular section has the shape of a third lateral surface of a truncated cone. The described most exact cone-shaped or truncated cone-shaped recess possible has the advantage that the recess can be configured in the body in an effective and particularly simple manner. Depending on the size of the recess and/or the mechanical machinability of the optically transparent material it is possible to use different methods, such as mechanical turning, compression or hot-stamping to produce the optical deflection element.

According to a further exemplary embodiment of the invention the first annular section, the second annular section and/or the third annular section has a curved surface. The respective surfaces can have a concave or convex surface independently of one another.

The described curvature in the individual annular sections has the advantage that the light beams exiting from the different slightly curved conical facets can be focused individually. In this process a convex optical interface of a facet results in slight focusing of the corresponding light structure. If there is focusing of the light structure on a circular line even without a concave interface, a slightly concave optical interface of a facet results in focal displacement of the corresponding light structure backward, in other words to a point that is further away from the light output side of the optical deflection element than the above-mentioned circular line.

According to a further exemplary embodiment of the invention the base body has the outer shape of a cylinder, in particular a circular cylinder. The described optical deflection element can thus be made from a so-called rod lens.

The base body of the optical deflection element preferably consists at least partially of a material having a high refractive index. This applies in particular to a wavelength of approximately 405 nm. This has the advantage that coherent light from standard semiconductor laser diodes can be fanned particularly significantly. Light with this comparatively short wavelength in the optical spectrum also has a much smaller depth of penetration into the human skin than light with a longer wavelength.

According to a further exemplary embodiment of the invention the light input side has a convex curvature. In this context convex curvature means that the light input side also has a contour that curves out in relation to the base body. In the case of a conventional contour in the manner of a cone surface this means that the center of curvature of the corresponding cone surface is on the side of the base body in relation to the light input side.

Convex curvature has the advantage that the refraction of the primary light beam bundle entering the base body on the light input side means that the primary light beam bundle is focused as a function of the degree of curvature. The curvature of the light input side can be tailored to the respective application here. If the light structures are projected onto the inner wall of an at least approximately cylindrical cavity, focusing can be set so that the light structures represent sharp illumination lines that are as fine as possible on the inner wall of the cavity to be measured.

According to a further exemplary embodiment of the invention the light input side has a curved first annular section and at least a curved second annular section. The respective surfaces here can have a concave or convex surface independently of one another.

Like the individual curvature of the annular sections on the light output side described above, the individual curvature of the individual annular sections on the light input side has the advantage that the light beams exiting from the different conical facets can be focused individually. In this process a convex optical interface of a facet results in slight focusing of the corresponding light structure. If there is focusing of the light structure to a circular line even without a convex interface, a slightly concave optical interface of a facet results in focal displacement of the corresponding light structure backward, in other words to a point that is further away from the light output side of the optical deflection element than the above-mentioned circular line.

Compared with the individual curvature of the annular sections on the light output side, the individual curvature of the individual annular sections on the light input side can be produced much more simply by means of conventional machining methods, such as mechanical turning, compression or hot-stamping. This is because compared with the light output side the light input side has a much simpler topology or surface structure, so the corresponding curvatures can be configured more easily.

According to a further exemplary embodiment of the invention the base body has a through opening, which extends coaxially to the optical axis.

This makes it possible for an optical observation system or camera to be passed through the optical deflection element. This is particularly advantageous if the optical deflection element is used for an optical measuring instrument with a compact structure, which is used to measure the size and/or shape of the cavity by spatial measurement of illumination lines projected onto the inner wall of a cavity.

According to a further exemplary embodiment of the invention the through opening is a drilled core having the shape of a cylinder disposed concentrically to the optical axis.

The described drilled core has the advantage that the optical deflection element can be produced particularly simply and therefore in a cost-saving manner.

The second independent claim describes an optical measuring device for the three-dimensional measuring of a cavity configured in an object, in particular for the three-dimensional measuring of the auditory canal of a human or animal. The optical measuring device has (a) a light source, set up to transmit illumination light along an illumination beam path, (b) an optical deflection element of the type mentioned above, which structures the transmitted illumination light spatially in such a manner that at least one illumination line running around the optical axis of the deflection element is produced on the inner wall, the shape of said illumination line being a function of the size and shape of the cavity, and (c) a camera, which captures the at least one illumination line at a triangulation angle by way of a mapping beam path.

The above-mentioned optical measuring device is based on the knowledge that cylindrically symmetrically structured illumination, which is projected into the inner wall of the cavity to be measured, allows three-dimensional (3D) measurement of the cavity in a simple manner using a modified triangulation method. The shape of the at least one illumination line is captured by the camera here, said camera preferably recording a two-dimensional (2D) image of the projection ring or projection rings symmetrically to the optical axis. It is possible to measure the inner wall of the cavity based in 3D on the deviations and/or distortions of the captured illumination line from symmetrical circular shapes concentric to the optical axis.

Compared with three-dimensional distance sensors, with which only one measuring point is illuminated and the height position of the illuminated measuring point is captured, the described optical measuring device has the advantage that a number of measuring points are measured almost simultaneously (automatically), being disposed around the optical axis. This significantly increases the scan rate overall.

A number of illumination structures are preferably produced, each of the illumination structures produced having the shape of a cone surface. This allows the number of measuring points that can be captured simultaneously by means of a single camera image to be increased further.

In the case of a cylindrical cavity, which extends symmetrically around the optical axis of the optical measuring device, illumination rings result, which are configured or disposed concentrically to the optical axis. In the case of a cylindrical cavity, which extends around a cylindrical axis having a parallel offset in relation to the optical axis of the optical measuring device, distorted illumination lines result, which have an elliptic shape in relation to the optical axis. Adjacent illumination lines in a first wall region of the inner wall, which is further away from the optical axis than a second wall region, are further away from one another. This is because the conical fanning of the individual illumination structures means that adjacent illumination lines are further away from one another, the further they are away from the optical axis. It is thus evident that both the deviation of the 3D form of the illumination lines captured by the camera from a perfect circle and the distance between adjacent illumination lines provide information about the 3D contour of the cavity.

It should be noted specifically here that an illumination structure or an, in some instances deformed, illumination line already contains 3D information relating to the size and shape of the cavity to be measured. Nevertheless it is advantageous, in particular for reasons of measuring speed and spatial resolution, to structure the illumination light transmitted by the light source into a number of conically widened illumination structures.

The capturing of the illumination lines at a triangulation angle means that the beam path of the mapping light and the beam path of the illumination light, i.e. the respective acceptance angle of the conical illumination structure, form an angle that is not 0°.

This angle is referred to as the triangulation angle. The greater this triangulation angle, the greater the accuracy of the 3D position determination.

The described optical measuring device has the advantage that no moving parts and in particular no moving optical components are required within the measuring device for 3D measurement. This means that the optical measuring device can be produced at comparatively low cost and that the reliability of the measuring device is also very good in actual deployment conditions.

It should be noted that the entire measuring device can preferably be displaced along the optical axis to measure larger cavities. The partial images recorded during such a movement can be put together again using appropriate image processing methods. Such putting together is frequently referred to as stitching.

According to one exemplary embodiment of the invention the optical measuring device also has an evaluation unit, which is connected downstream of the camera and is set up so that it is possible to determine the size and shape of at least part of the cavity automatically by processing the image of the at least one illumination line captured by the camera.

The described evaluation unit thus advantageously allows automatic image evaluation of the 2D images captured by the camera, so that 3D data of the measured cavity can be supplied directly as the output variable of the optical measuring device for further data processing.

According to a further exemplary embodiment of the invention the optical measuring device also has an optical projection system, which is disposed in the illumination beam path. This has the advantage that it is possible to focus the illumination light, optionally in combination with a suitable curvature of the essentially conical facets of the light output side, so that the illumination lines are mapped as sharply as possible on the inner wall of the cavity to be measured and can therefore be captured as sharp structures by the camera.

The optimal selection of the focal length of this optical system is therefore a function of the fanning of the illumination beam striking the optical system, the optical path length of the illumination light between the optical system and the optical deflection element and the optical path length between the optical deflection element and the inner wall. The focal length of this optical system should therefore be a function not only of the design of the described optical measuring device but also of the approximate anticipated size of the cavity to be measured.

It should be noted that the convex curvature of the light input side of the base body described above in conjunction with an exemplary embodiment of the optical deflection system also has the same qualitative effect as the optical projection system described here. The same also applies to the curvatures of the essentially conical facets on the light output side.

According to a further exemplary embodiment of the invention the optical measuring device also has a beam splitter disposed at an oblique angle in the optical axis of the deflection element. This beam splitter deflects the illumination beam path in such a manner that either (a) an object-side section of the illumination beam path runs parallel to the optical axis or (b) an image-side section of the mapping beam path runs at an angle to the optical axis.

In this context an oblique angle means that the beam splitter is disposed at an angle not equal to 0° and not equal to 90° in relation to the optical axis. The beam splitter is preferably inclined at an angle of 45° to the optical axis, so that the illumination beam path or the mapping beam path has a 90° bend.

According to a further exemplary embodiment of the invention at least one section of the illumination beam path, in which the illumination light is passed parallel to the optical axis, is shaped around the mapping beam path running in the center of the optical axis.

The illumination beam path here can be disposed around the optical axis or mapping beam path with annular symmetry or concentrically to the optical axis in cross-section. This means that an illumination beam concentric to the optical axis strikes the optical deflection element, which is likewise configured symmetrically to the optical axis. The refractive optical deflection element having a drilled core described above is an appropriate optical deflection element for example.

It should be noted that the illumination beam path and the mapping beam path can also run coaxially to some degree. For the 3D measurement based on the triangulation principle it is sufficient if the illumination beam path and the mapping beam path are spatially separated on the object side, i.e. in proximity to the illumination lines to be measured, so that a triangulation angle is defined. An object-side branching of the illumination beam path and mapping beam path can be effected for example by appropriate beam splitters or by an optical waveguide, the object-side end of which is split into two spatially separate sub-ends.

According to a further exemplary embodiment of the invention the optical measuring device also has a light-conducting facility, which is disposed in the mapping beam path and which is set up to transmit a two-dimensional image of the illumination lines to the camera.

A mechanically relatively rigid rod lens arrangement, as used in endoscopes for example, can be used as the light-conducting facility. An endoscopic system based on a graded optical system can also be used as the light-conducting facility, the refractive index changing as a function of radius. It is thus possible to achieve curvature of the light beams within the light-conducting facility so that the camera can capture mapping beams from a wide angle range as a result.

A so-called Hopkins optical system can also be used as the light-conducting facility, this also being a mechanically largely rigid optical arrangement. A Hopkins optical system can be a type of glass tube for example, in which air lenses are inserted to give a particularly detailed view during endoscopic examinations. This advantage of the particularly detailed view also results with the described optical measuring device in a particularly high level of accuracy and reliability for the 3D measurement.

A so-called image waveguide, which comprises a number of individual optical waveguides or glass fibers, is also suitable as a light-conducting facility. An image waveguide has the advantage of flexibility, so that the optical measuring device can be realized with an at least partially flexible structure. This allows accurate cavity measurement even in curved cavities, into which a rigid measuring device cannot be inserted.

The third independent claim describes a method for producing a concentrically fanned, spatially structured light beam bundle. The method has the following steps: transmission of a primary light beam bundle to an optical deflection element as described above, so that the primary light beam bundle enters the base body of the optical deflection element on the light input side and exits from the base body as a secondary light beam bundle on the light output side. In this process the secondary light beam bundle has a light structure at least in the shape of a cone surface.

The above-mentioned method is based on the knowledge that use of the refractive optical deflection element described above allows broad fanning of the secondary light beam bundle to be realized particularly simply compared with the use of known diffractive optical deflection elements. Broad fanning means that the corresponding cone surfaces have a large acceptance angle.

If the light output side of the base body has a number of annular sections with differently inclined, essentially conical facets, the corresponding cone tips of the fanned light cones can coincide at an actual source point, which is on the optical axis. In this context an actual source point means that the illumination structures start at least approximately from one source point on the optical axis.

If the base body, as described above in a preferred exemplary embodiment, has a through opening or drilled core, the secondary light beam bundle exits from at least a circular section, which is disposed concentrically around the optical axis. In this instance too the corresponding cone tips can be seen as an actual source point of the secondary light beam bundle which is fanned in the shape of a cone surface.

BRIEF DESCRIPTION OF THE DRAWINGS

Further advantages and features of the present invention will emerge from the exemplary description which follows of currently preferred embodiments. The individual figures in the drawing accompanying this application should only be considered to be schematic and not to scale.

FIG. 1a shows a cross-sectional view of an optical measuring device according to one exemplary embodiment of the invention.

FIG. 1b shows a camera image with four images of illumination lines projected onto the inner wall of a cavity to be measured.

FIG. 1c shows a front view of the object-side end of the optical measuring device shown in FIG. 1a.

FIG. 2 shows the beam paths of the illumination light and mapping light configured at the object-side end of the optical measuring device shown in FIG. 1a, said beam paths determining the triangulation angle.

FIG. 4b shows a structural diagram of the optical deflection element shown in FIG. 4a.

FIG. 4c shows a simulation of the refractive production of two light structures in the shape of a cone surface using the optical deflection element shown in FIG. 4a.

FIG. 6 shows an optical deflection element, wherein the annular sections each have a convex curvature on the light output side.

FIG. 7 shows an optical deflection element, wherein the light input side has two curved annular sections, each with a convex curvature.

DETAILED DESCRIPTION OF THE INVENTION

Figure 3:
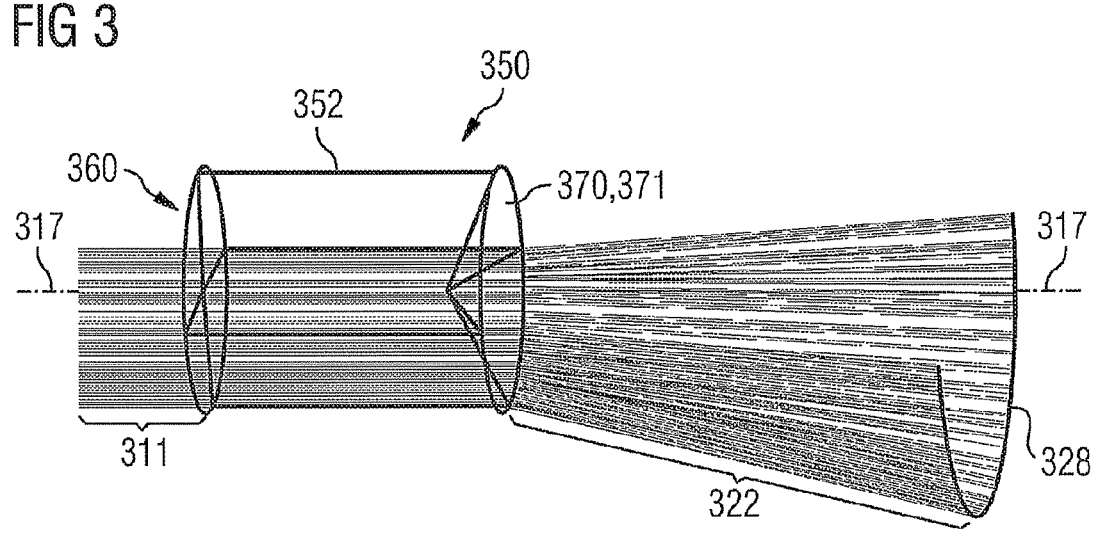
FIG. 3 shows a simulation of the refractive production of an individual light structure in the shape of a cone surface.

It should be noted here that the reference characters for identical or corresponding components only differ in the first figure in the drawing.

FIG. 1a shows a cross-sectional view of an optical measuring device 100 according to one exemplary embodiment of the invention. The optical measuring device 100 has a cylindrically symmetrical shape in relation to an optical axis 117.

The optical measuring device 100 has a light source 110, which is a laser diode 110 according to the exemplary embodiment shown here. Of course other light sources can also be used, for example a light-emitting diode. The laser diode 110 emits monochromatic illumination light 111, which strikes an optical projection system 112, which widens the illumination beam 111. The widened illumination beam 111 strikes a beam splitter 113, which is oriented at an angle of 45° in relation to the optical axis 117, so that at least some of the illumination light 111 is coupled into a hollow cylinder 115 as a function of the reflective capacity of the beam splitter 113, said hollow cylinder 115 being disposed symmetrically in relation to the optical axis 117. To prevent the illumination light 111 being coupled into the central part of the hollow cylinder 115, an optical shading element 114 is disposed between the beam splitter 113 and the laser diode 110.

The illumination light deflected by the beam splitter 113 is guided by the hollow cylinder 115 in an illumination beam path 116. The illumination beam path 116 is configured as cylindrically symmetrical in relation to the optical axis 117. At an object-side end of the optical measuring device 100 the illumination light strikes an optical deflection element 150, which likewise has a cylindrically symmetrical shape and is disposed in a cylindrically symmetrically manner around the optical axis 117. According to the exemplary embodiment shown here the optical deflection element 150 is an optically refractive element, which is described in more detail below with reference to FIGS. 3, 4a and 4b.

The optical deflection element 150 structures the illumination light spatially in such a manner that a number of illumination structures result concentric to the optical axis 117, each having the shape of a cone surface 122 and being projected onto the inner wall of a cavity 125 to be measured. Only one illumination structure 122 is shown in FIG. 1a for reasons of clarity.

It should be noted that the camera 145 and the laser diode 110 can also be swapped when using a corresponding beam splitter 113. A transmission-selective glass plate for example can be used as a beam splitter, being metal-coated within a small elliptical region in the center such that the image in the center of the illumination beam path 116 is coupled out rather than the laser beam.

According to the exemplary embodiment shown here the cavity to be measured is an auditory canal 125 of a patient. The auditory canal 125 typically has a diameter d of approximately 4 mm.

It should however be pointed out that the measuring device 100 can also be used to measure other cavities. Thus for example the three-dimensional shape of drilled holes can be measured in an exact manner before precisely fitting rivets can be selected for a particularly reliable riveted connection, in aviation construction for example.

The projection of the illumination structure 122 onto the inner wall of the cavity 125 produces a closed illumination line 128, the shape of which is a function of the size and shape of the cavity 125. The sharpness of the illumination lines 128 here is a function of the focusing of the illumination structures 122 on the inner wall. The focal length of the optical projection system 112 can thus be adjusted so that sharp illumination lines 128 are produced on the inner wall of the cavity for an approximate anticipated size of the cavity to be measured.

The size and shape of the individual illumination lines 128 are captured by a camera 145. This is done by way of a mapping light 130 from the illumination lines 128. This mapping light 130 is converged by means of an optical mapping system 132, which has a particularly short focal length. The optical mapping system 132 can also be referred to as a fish eye due to its extremely wide acceptance angle.

The mapping light 130 converged by the optical mapping system 132 is guided by means of a light-conducting facility 135 to the image-side end of the optical measuring device 100. According to the exemplary embodiment shown here the light-conducting facility is a rod lens arrangement 135, which is also used for example in endoscopic devices in medical engineering. The second optical mapping system can be configured as a single piece with the rod lens arrangement 135, in that the corresponding end face interface of a corresponding rod lens facing the cavity has an extremely severe curvature.

The rod lens arrangement 135 has a number of individual rod lenses 135*a*, which together produce a length 1 of approximately 50 mm. The rod length arrangement 135 can of course also be of any other length. The rod lens arrangement can also be a so-called Hopkins lens arrangement.

The rod lens arrangement 135 therefore defines a mapping beam path 136, which extends along the optical axis 117 to the image-side end of the optical measuring device 100. The mapping beam path 136 and the illumination beam path 116 are each disposed in a cylindrically symmetrical manner in relation to the optical axis 117, with the illumination beam path 116 outside the mapping beam path 136.

Of course the optical measuring device can also have a structure in which the mapping beam path runs outside the illumination beam path. In any case there must be a spatial separation of illumination light 122 and mapping light 130 at the latest at the object-side end of the measuring device 100, so that the projected illumination lines 128 can be captured at a triangulation angle and the 3D contour of the cavity 125 can thus be determined. A triangulation angle is always present when the illumination, in other words here the production of the illumination lines 128, takes place at a different angle from the observation, in other words here the mapping of the illumination lines 128 toward the camera 145.

The mapping light 130 guided in the rod lens arrangement 135 strikes the beam splitter 113. The beam splitter is penetrated by at least some of the mapping light 130 only with a certain parallel offset. This parallel offset is a function of the thickness, the refractive index and the angular position of the beam splitter 113 relative to the optical axis 117. The remaining part of the mapping light 130 is reflected at the beam splitter and strikes the optical shading element 114 and/or the laser diode 110 as lost light.

The part of the mapping light 130 passing through the beam splitter strikes an optical mapping system 142 and is mapped by this onto the camera 145. The camera 145 therefore records a camera image 148, which shows images 149 of the illumination lines 128 as a function of the shape of the cavity 125, these being distorted in particular in the peripheral region of the camera image 148. FIG. 1*b* shows an example of such a camera image 148, in which a total of four images 149 of corresponding illumination lines 128 projected onto the inner wall of the cavity 125 can be seen. A quantitative analysis of this distortion carried out in an evaluation unit 146 downstream of the camera 145 allows the shape and size of the cavity 125 to be determined.

FIG. 1*c* shows a front view of the object-side end of the optical measuring device 100. The optical mapping system 132, which is enclosed by the optical deflection element 150 is clearly shown.

FIG. 2 shows a cross-sectional diagram of beam paths of the illumination light 222 and the mapping light 230 configured at the object-side end of the optical measuring device 100 now shown with the reference character 200. A mean projection or illumination angle $\beta$ results for a specific illumination line 228, as shown in FIG. 1*d*, in relation to the optical axis 217.

The optical deflection element 250 has a mean radial distance r from the optical axis 217. A mapping angle $\alpha$ correspondingly results for the illumination line 228 shown in relation to the optical axis 217. It is taken into account here that the mapping light 230 is converged by the optical mapping system 232 disposed in the center of the optical axis 217.

The triangulation angle $\theta$ results from the difference between the two angles $\alpha$ and $\beta$ ($\theta=\alpha-\beta$). As shown in FIG. 1*d* this triangulation angle $\theta$ is of course also a function of the longitudinal distance $\Delta 1$. This longitudinal distance $\Delta 1$ results from the distance parallel to the optical axis 217 between the deflection element 250 and the optical mapping system 232.

FIG. 3 shows a simulation of the refractive production of an individual light structure 322 in the shape of a cone surface. A primary light beam bundle 311 passes through a light input side 360 into the base body 352 of the optical deflection element 350. The light output side 370 opposite the light input side 360 has a conical facet 371, so that a cone-shaped recess is configured in the base body. The light beam bundle penetrating the base body is widened to form the illumination structure 322 with the shape of a cone surface at the optical interface inclined correspondingly in relation to an optical axis 317 of the deflection element 350. An illumination line 328 thus results on a cylindrical inner surface (not shown) of a cavity to be measured.

Figure 4A:
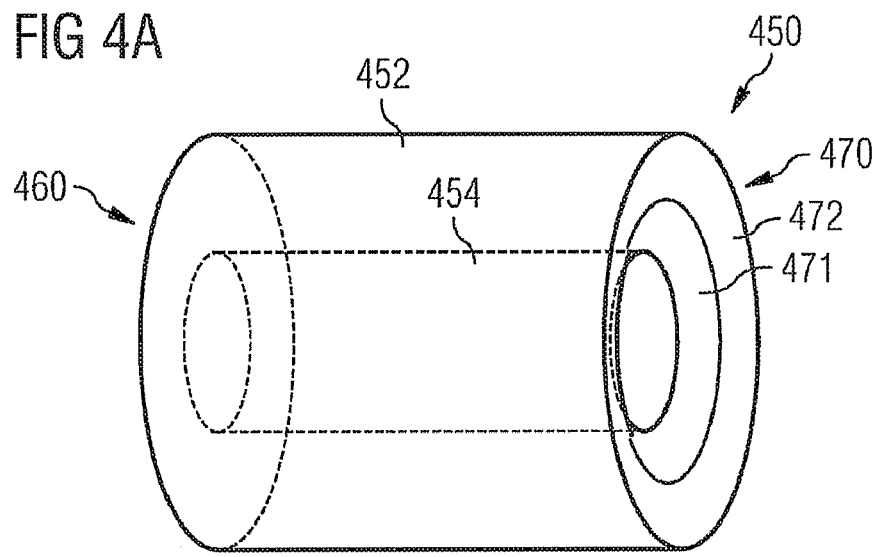
FIG. 4a shows a perspective view of an optical deflection element, having two conical facets.
Figure 4B:
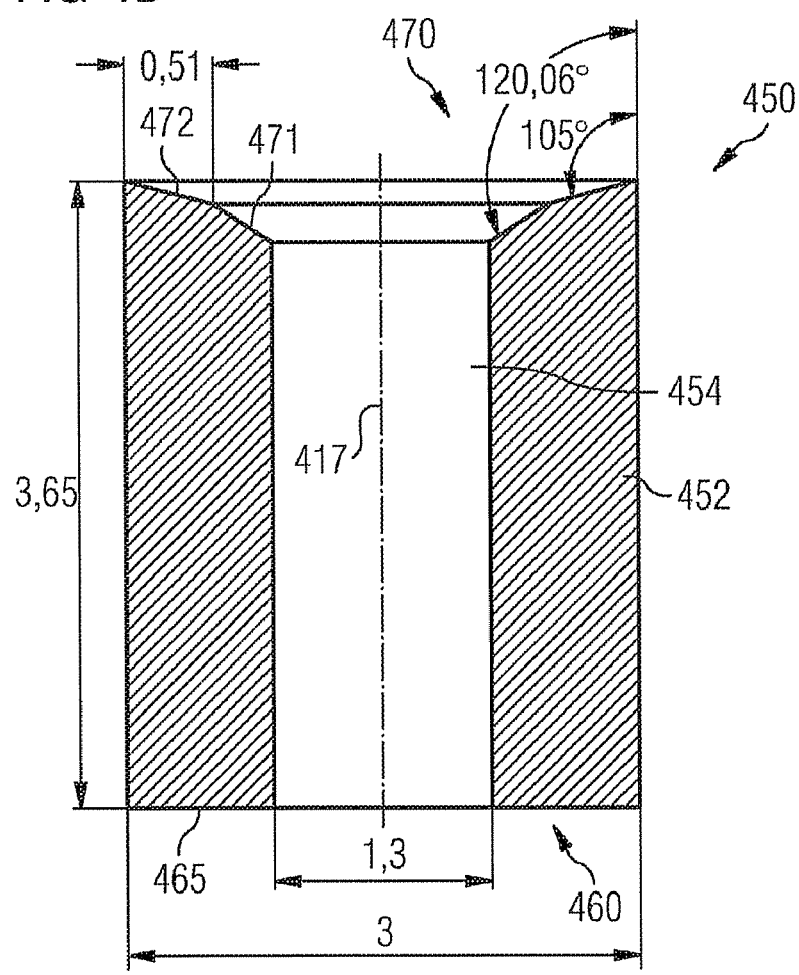

FIGS. 4*a* and 4*b* show an optical deflection element 450, which has two conical facets, a first conical facet 471 configured in a first annular section and a second conical facet 472 configured in a second annular section. FIG. 4*a* shows a perspective view of the optical deflection element 450, while FIG. 4*b* shows a structural diagram of the optical deflection element 450.

The optical deflection element 450 has an essentially cylindrical base body 452, in which a through opening 454 is configured. According to the exemplary embodiment shown here the base body 452 has a diameter of 3 mm and a length of 3.65 mm. The through opening 454 configured as a drilled hole has a diameter of 1.3 mm. The deflection element 450 can of course also be realized with different dimensions.

An end-face light input side 460 has a slight convex curvature 465 with a radius of curvature of 30 mm. This curvature 465 thus represents a slightly focusing optical interface for a primary light beam bundle entering on the light input side 460. Like the entire base body 452 the convex shaped input interface has a rotationally symmetrical shape in relation to the optical axis 417.

The light output side 470 opposite the light input side 460 has a concave contour, which is determined by the two conical facets 471 and 472. As shown in FIG. 4*b* the second conical facet 472 has a radial thickness of 0.51 mm in relation to the optical axis 417. The optical interface of the second conical facet 472 is also inclined at an angle of 105° in relation to the optical axis 417. The first conical facet 472 is inclined at an angle of 120.06° in relation to the optical axis 417. Other dimensions and/or angles are of course possible here too.

Figure 4C:
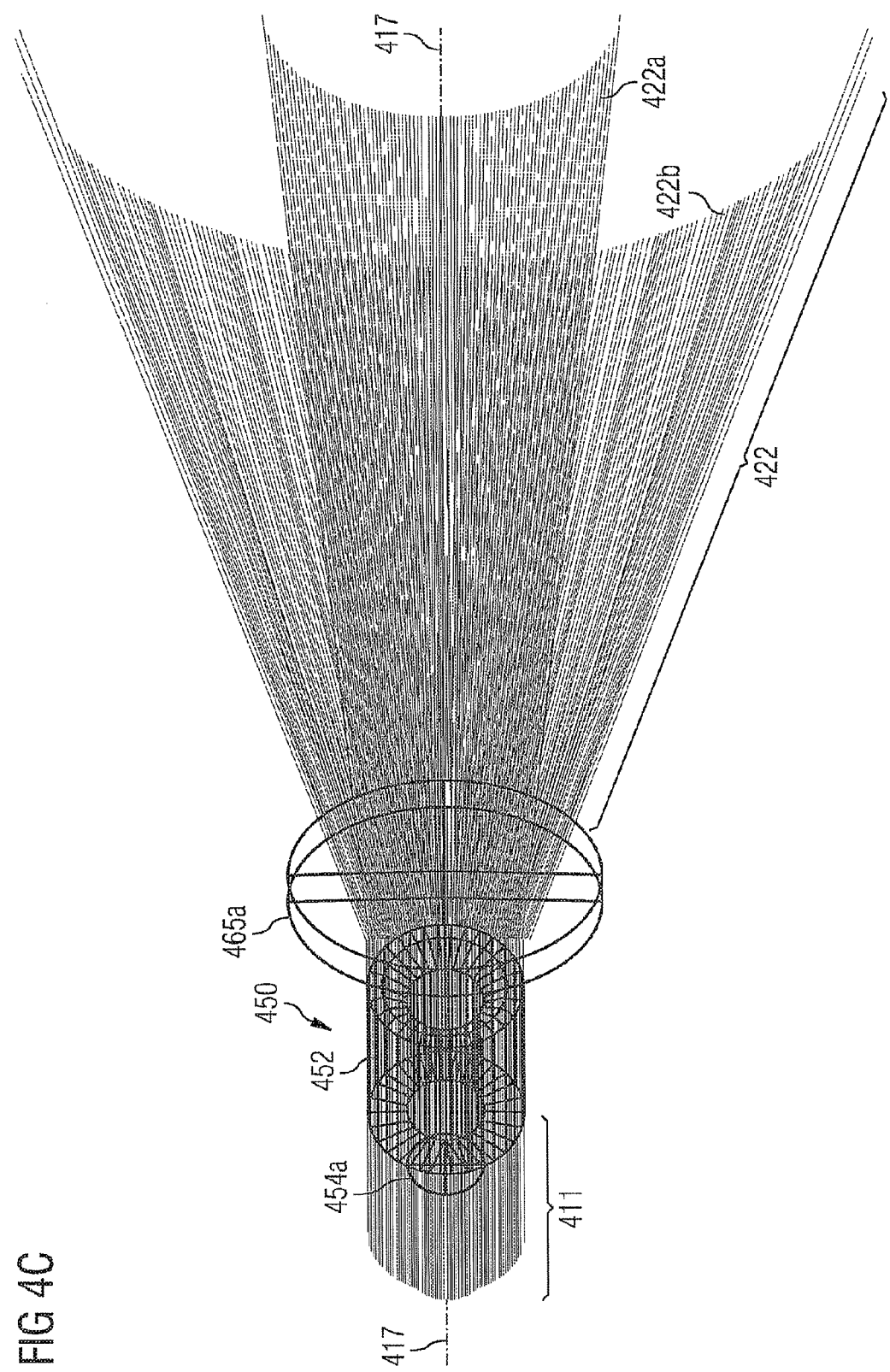

FIG. 4c shows a simulation of the refractive production of two light structures in the shape of a cone surface using the optical deflection element 450. A primary light beam bundle 411 strikes the base body 452 of the deflection element 450 parallel to the optical axis 417. The through hole 454 shown in FIGS. 4a and 4b is taken into account by a circular shading element 454a in the simulation. The shading element 454a is disposed concentrically to the optical axis 417.

The concave curvature 465 of the light input side 460 is simulated by a converging lens 465a, which is likewise disposed concentrically to the optical axis 417 directly behind the base body 452. The two conical facets 471 and 472 bring about a cylindrically symmetrical branching of the primary light beam bundle 411 into a secondary light beam bundle 422, which has a first light structure 422a in the shape of a cone surface and a second light structure 422b in the shape of a cone surface.

Figure 5:
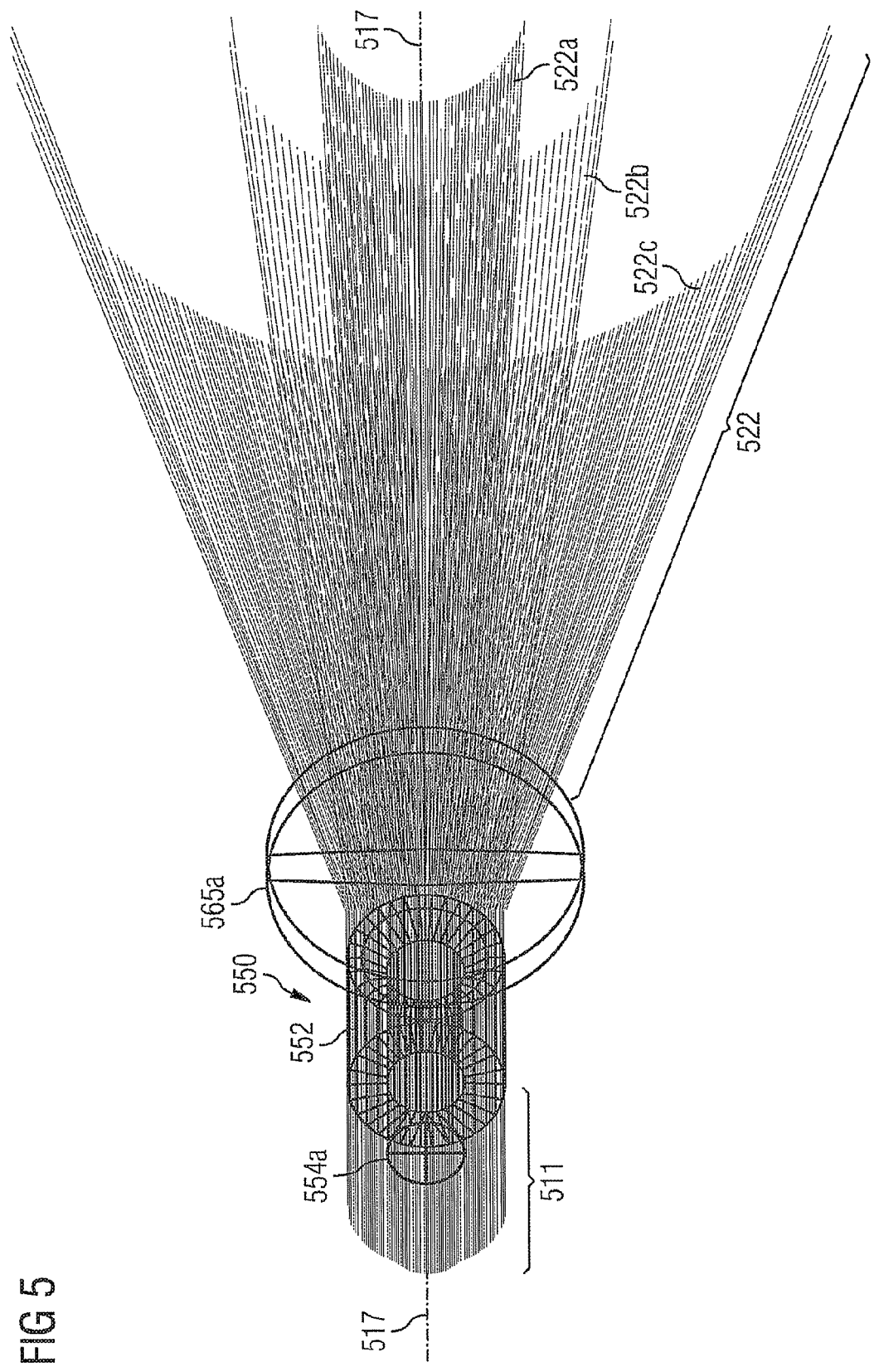
FIG. 5 shows a simulation of the refractive production of three light structures in the shape of a cone surface, which are produced by an optical deflection element with three conical facets.

FIG. 5 shows a simulation of the refractive production of three light structures 522a, 522b and 522c in the shape of a cone surface, which are produced by an optical deflection element 550 with three conical facets. In the simulation shown a primary light beam bundle 511 strikes a base body 552 parallel to an optical axis 517. A through hole is simulated by a circular shading element 554a, which is disposed concentrically to the optical axis 517.

Concave curvature of the light input side of the optical deflection element 550 is simulated by a converging lens 565a, which is likewise disposed concentrically to the optical axis 517 and directly behind the base body 552. The three conical facets bring about a cylindrically symmetrical branching of the primary light beam bundle 511 into a secondary light beam bundle 522, which has the first light structure 522a in the shape of a cone surface, the second light structure 522b in the shape of a cone surface and the third light structure 522c in the shape of a cone surface.

It should be noted that only half of the simulations shown in FIGS. 3, 4c and 5 are illustrated so that the resulting widened light cones can be shown more clearly. In the context of the corresponding simulations this halving of the diagram was achieved using a suitable rectangular shutter in the respective beam path.

FIG. 6 shows an optical deflection element 650 according to a further exemplary embodiment of the invention. Like the deflection elements described above the deflection element 650 has a base body 652 with a drilled core 654, shaped with rotational symmetry in relation to an optical axis 617. The light input side 660 has a flat interface. The light output side 670 has two annular sections shaped symmetrically in relation to the optical axis 617, a first annular section 671 and a second annular section 672.

It should be noted that the annular sections 671 and 672 each have a gentle curvature, which is shown in a greatly exaggerated manner in FIG. 6. The large radius of curvature means that the corresponding surface contours can be described as before as essentially conical facets. The curvature of the essentially conical facet 671 may be different from the curvature of the essentially conical facet 672. It is thus possible to focus the light beams exiting from the different slightly curved conical facets individually.

FIG. 7 shows an optical deflection element 750 according to a particularly preferred exemplary embodiment of the invention. The deflection element 750 also has a base body 752 with a drilled core 754, which is shaped with rotational symmetry in relation to an optical axis 717. In contrast to the exemplary embodiment shown in FIG. 6 the light input side 760 has a structured surface contour, which comprises two annular sections shaped symmetrically in relation to the optical axis 717, a first annular section 761 and a second annular section 762. The annular sections 771 and 772 on the light output side have no further curvature at the two conical facets.

The radii of the individual annular sections 761, 762, 771, 772 are tailored to one another such that when illumination strikes parallel to the optical axis 717, the first annular section 761 is assigned to the first annular section 771 and the second annular section 762 is assigned to the second annular section 772. Therefore the light beams exiting from the different conical facets 771 and 772 can be focused individually due to a corresponding curvature of the annular sections 761 and 762.

It should be noted that the two exemplary embodiments shown in FIG. 6 and FIG. 7 can also be combined with one another so that the annular sections each have an individual curvature both on the light input side and on the light output side.

It should be noted that the embodiments described here only represent a limited selection of possible variants of the invention. It is thus possible to combine the features of individual embodiments in an appropriate manner so that the person skilled in the art will consider a plurality of different embodiment to be disclosed in an evident manner with the variants set out explicitly here.

The invention claimed is:

1. An optical deflection element for a refractive production of a spatially structured light beam bundle concentrically fanned to an optical axis of the deflection element, comprising:
   a base body that is made of an optically transparent material,
   wherein the base body comprises:
      a light input side that couples a primary light beam bundle into the base body; and
      a light output side that has a cylindrically symmetrical contour in relation to the optical axis defining a recess in the base body and exits the primary light beam bundle as the spatially structured light beam bundle,
   wherein the contour has a first annular section,
   wherein the first annular section has a shape of at least a part of a first lateral surface of a cone pointing into an interior of the base body, and
   wherein lateral lines of the first lateral surface forms a first angle with the optical axis.

2. The optical deflection element as claimed in claim 1,
   wherein the contour has a second annular section that is disposed outside the first annular section in a radial direction,
   wherein the second annular section has a shape of a second lateral surface of a truncated cone, and
   wherein lateral lines of the second lateral surface forms a second angle with the optical axis that is different from the first angle.

3. The optical deflection element as claimed in claim 2,
   wherein the contour has a third annular section that is disposed outside the second annular section in a radial direction,
   wherein the third annular section has a shape of a third lateral surface of the truncated cone, and
   wherein lateral lines of the third lateral surface forms a third angle with the optical axis that is different from the second angle.

4. The optical deflection element as claimed in claim 3, wherein an angular difference between the first angle and a right angle is greater than an angular difference between the second angle and a right angle.

5. The optical deflection element as claimed in claim 3, wherein an angular difference between the first angle and a right angle is smaller than an angular difference between the second angle and a right angle.

6. The optical deflection element as claimed in claim 3, wherein the first annular section, the second annular section, and the third annular section has a curved surface.

7. The optical deflection element as claimed in claim 1, wherein the base body has an outer shape of a the cylinder, and
wherein the cylinder is a circular cylinder.

8. The optical deflection element as claimed in claim 1, wherein the light input side has a convex curvature.

9. The optical deflection element as claimed in claim 1, wherein the light input side has a curved first annular section and at least a curved second annular section.

10. The optical deflection element as claimed in claim 1, wherein the base body has a through opening extending coaxially to the optical axis.

11. The optical deflection element as claimed in claim 10, wherein the through opening is a drilled core having a shape of a cylinder disposed concentrically to the optical axis.

12. An optical measuring device for three-dimensionally measuring a cavity in an object, comprising:
a light source that transmits an illumination light along an illumination beam path;
an optical deflection element that spatially structures the transmitted illumination light and produces an illumination line running around an optical axis of the optical deflection element on an inner wall with a shape as a function of a size and a shape of the cavity; and
a camera that captures the illumination line at a triangulation angle by a mapping beam path,
wherein the optical deflection element comprises a base body that is made of an optically transparent material,
wherein the base body comprises:
a light input side that couples a primary light beam bundle into the base body; and
a light output side that has a cylindrically symmetrical contour in relation to the optical axis defining a recess in the base body and exits the primary light beam bundle as the spatially structured light beam bundle,
wherein the contour has a first annular section,
wherein the first annular section has a shape of at least a part of a first lateral surface of a cone pointing into an interior of the base body, and
wherein lateral lines of the first lateral surface forms a first angle with the optical axis.

13. The optical measuring device as claimed in claim 12, further comprising an evaluation unit that is connected downstream of the camera and determines the size and the shape of the cavity by processing an image of the illumination line captured by the camera.

14. The optical measuring device as claimed in claim 12, further comprising an optical projection system that is disposed in the illumination beam path.

15. The optical measuring device as claimed in claim 12, further comprising a beam splitter that is disposed at an oblique angle in the optical axis, wherein the beam splitter:
deflects the illumination beam path so that an object-side section of the illumination beam path runs parallel to the optical axis, or
deflects the mapping beam path so that an image-side section of the mapping beam path runs at an angle to the optical axis.

16. The optical measuring device as claimed in claim 12, wherein the illumination light is passed parallel to the optical axis along the illumination beam path and a section of the illumination beam path is shaped around the mapping beam path running in a center of the optical axis.

17. The optical measuring device as claimed in claim 12, further comprising a light-conducting unit that is disposed in the mapping beam path and transmits a two-dimensional image of the illumination line to the camera.

18. The optical measuring device as claimed in claim 12, wherein the cavity is an auditory canal of a human or animal.

19. A method for producing a concentrically fanned and spatially structured light beam bundle, comprising:
transmitting a primary light beam bundle to an optical deflection element;
directing the primary light beam bundle entering a base body of the optical deflection element on a light input side of the optical deflection element;
exiting the primary light beam bundle from the base body of the optical deflection element on a light output side as a secondary light beam bundle having a cone surface light structure; and
producing the concentrically fanned and spatially structured light beam bundle in relation to an optical axis of the optical deflection element from the secondary light beam bundle,
wherein the light output side has a cylindrically symmetrical contour in relation to the optical axis defining a recess in the base body,
wherein the contour has a first annular section,
wherein the first annular section has a shape of at least a part of a first lateral surface of a cone pointing into an interior of the base body, and
wherein lateral lines of the first lateral surface forms a first angle with the optical axis.

* * * * *